US008323524B2

(12) United States Patent
Flynn et al.

(10) Patent No.: US 8,323,524 B2
(45) Date of Patent: Dec. 4, 2012

(54) APPARATUS INCLUDING HYDROFLUOROETHER WITH HIGH TEMPERATURE STABILITY AND USES THEREOF

(75) Inventors: Richard M. Flynn, Mahtomedi, MN (US); Michael G. Costello, Afton, MN (US); Michael J. Bulinski, Houlton, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 426 days.

(21) Appl. No.: 12/571,542

(22) Filed: Oct. 1, 2009

(65) Prior Publication Data

US 2011/0079043 A1 Apr. 7, 2011

(51) Int. Cl.
*C09K 5/04* (2006.01)
*F25B 1/00* (2006.01)
(52) U.S. Cl. ........ 252/67; 62/502; 165/104.19; 568/615
(58) Field of Classification Search ............... 252/67; 62/502; 165/104.19; 568/615
See application file for complete search history.

(56) References Cited

U.S. PATENT DOCUMENTS

| | | | |
|---|---|---|---|
| 2,713,593 A | 7/1955 | Brice et al. | |
| 3,242,218 A | 3/1966 | Miller | |
| 3,699,145 A | 10/1972 | Sianesi et al. | |
| 3,962,348 A | 6/1976 | Benninger et al. | |
| 5,750,797 A | 5/1998 | Vitcak et al. | |
| 6,043,201 A * | 3/2000 | Milbrath et al. | 508/582 |
| 6,374,907 B1 | 4/2002 | Tousignant et al. | |
| 6,923,921 B2 | 8/2005 | Flynn et al. | |
| 7,128,133 B2 * | 10/2006 | Costello et al. | 165/80.4 |
| 7,390,427 B2 | 6/2008 | Costello et al. | |
| 2003/0039919 A1 | 2/2003 | Bradley et al. | |
| 2007/0051915 A1 * | 3/2007 | Day | 252/8.62 |
| 2007/0051916 A1 * | 3/2007 | Flynn et al. | 252/71 |
| 2007/0054186 A1 * | 3/2007 | Costello et al. | 429/200 |
| 2007/0267464 A1 | 11/2007 | Vitcak et al. | |
| 2008/0139683 A1 | 6/2008 | Flynn et al. | |
| 2011/0257073 A1 * | 10/2011 | Flynn et al. | 510/499 |

FOREIGN PATENT DOCUMENTS

EP  0 557 167 A1  8/1993

OTHER PUBLICATIONS

CAS reg. No. 1284215-35-5, Apr. 22, 2011.*
Tasaki, "Solvent Decompositions and Physical Properties of Decomposition Compounds in Li-Ion Battery Electrolytes Studies by DFT Calculations and Molecular Dynamics Simulations," *J. Phys. Chem. B*, 109 pp. 2920-2933, (2005).
A. A. Il'in et al., Promising Prospects for Using Partially Fluorinated Alcohols as O-Nucleophilic Reagents in Organofluoric Synthesis, *Russian Journal of Applied Chemistry*, vol. 80, No. 3, pp. 405-418 (2007).
G. Marchionni et al., The Comparison of Thermal Stability of Some Hydrofluoroethers and Hydrofluoropolyethers, *J. Fluorine Chem.*, 125, pp. 1081-1086 (2004).
Naoaki Yakata et al., Influence of Dispersants on Bioconcentration Factors of Seven Organic Compounds With Different Lipophilicities and Structures, *Chemosphere*, 64, pp. 1885-1891 (2006).
R. E. Banks, ed., Preparation, Properties, and Industrial Applications of Organofluorine Compounds, Halsted Press, pp. 19-43 (1982).
A. V. Fokin et al., Reaction of Polyfluorinated Alcohols With Fluoroolefins, *Izvestiya Akademii Nauk SSR, Seriya Khimicheskaya*, No. 9, pp. 2141-2146 (1977).
U.S. Appl. No. 12/263,661, Richard M. Flynn, Michael J. Bulinski, Michael G. Costello, Nov. 3, 2008.

* cited by examiner

*Primary Examiner* — Douglas McGinty

(57) ABSTRACT

An apparatus is provided that includes a device and a mechanism for heat transfer that includes a provided hydrofluoroether having high temperature stability. Also provided is a method of transferring heat and a composition that includes a provided hydrofluoroether.

11 Claims, No Drawings

US 8,323,524 B2

APPARATUS INCLUDING HYDROFLUOROETHER WITH HIGH TEMPERATURE STABILITY AND USES THEREOF

FIELD

The present disclosure broadly relates to heat transfer fluids and their use in devices.

BACKGROUND

Hydrofluoroether compounds (HFEs) comprise a class of commercially valuable chemical compounds. In a number of applications, hydrofluoroethers have been found to be useful as replacements for chlorofluorocarbons (CFCs), which are currently disfavored and regulated due to the adverse effects that CFCs are believed to have on the environment. Unlike CFCs, hydrofluoroether compounds that contain fluorine as the only halogen have essentially no effect on the earth's ozone layer. Such hydrofluoroether compounds are thus said to exhibit an "ozone depletion potential" of zero. In addition, such HFEs are typically more easily degraded within the earth's atmosphere, which results in a low global warming potential.

The term hydrofluoroether, as used in the art, commonly refers to those ethers having partial substitution of hydrogen atoms by fluorine atoms. Some hydrofluoroethers are commercially available. Examples include those hydrofluoroethers available under the trade designations 3M NOVEC ENGINEERED FLUID 7000, 7100, 7200, 7300, 7500, and 7600 from 3M Company of Saint Paul, Minn. Hydrofluoroethers have been used in applications such as cleaning solvents, deposition solvents, battery electrolyte solvents, and heat transfer media. The uses of hydrofluoroethers can be limited by their thermal stability.

SUMMARY

Some hydrofluoroethers have been disclosed as heat-transfer fluids. However, there is a continuing need for heat-transfer fluids that are inert, have high dielectric strength, low electrical conductivity, chemical inertness, thermal stability, and effective heat transfer, are liquid over a wide temperature range, have good heat-transfer properties over a wide range of temperatures and also have reasonably short atmospheric lifetimes so as to limit their global warming potential.

Thermally stable hydrofluorocarbons can meet many of these needs. Solvent systems that include hydrofluorocarbons can provide materials that do not break down during long term usage at temperatures greater than about 150° C. Heat transfer fluids with low toxicity and low global warming potential can be useful for heat transfer, for example, in the electronics industry.

In one aspect, an apparatus is provided that requires heat transfer that includes a device and a mechanism for transferring heat to or from the device, the mechanism comprising a heat transfer fluid represented by the following structure: $H(C_2F_4)_xCH_2OCF_2CFH-Y-R_f$ wherein Y is a single bond or a single oxygen atom, and x=1-3, wherein when Y is a single bond, then $R_f$ is selected from $CF_3$, $C_2F_5$, and $n-C_3F_7$, wherein, when Y is a single oxygen atom, then $R_f$ is a linear, branched, or cyclic perfluoroaliphatic group of 1 to 7 carbon atoms which may, independently, contain one or more catenated heteroatoms such as nitrogen or oxygen, and wherein the total number of carbon atoms in the structure is greater than or equal to 9.

In another aspect, a composition is provided that includes a fluid represented by the following structure: $H(C_2F_4)_xCH_2OCF_2CFH-O-R_f$ wherein x=1-3, wherein, $R_f$ is a linear, branched, or cyclic perfluoroaliphatic group of 1 to 7 carbon atoms which may, independently, contain one or more catenated heteroatoms such as nitrogen or oxygen, and wherein the total number of carbon atoms in the structure is greater than or equal to 9.

In yet another aspect, a method of heat transfer is provided that includes the steps of providing a device and a mechanism for transferring heat to or from the device; the mechanism comprising a heat transfer fluid represented by the following structure, $H(C_2F_4)_xCH_2OCF_2CFH-Y-R_f$, wherein Y is a single bond or a single oxygen atom, and x=1-3, wherein when Y is a single bond, then $R_f$ is selected from $CF_3$, $C_2F_5$, and $n-C_3F_7$, wherein, when Y is a single oxygen atom, then $R_f$ is a linear, branched, or cyclic perfluoroaliphatic group of 1 to 7 carbon atoms which may, independently, contain one or more catenated heteroatoms such as nitrogen or oxygen, and wherein the total number of carbon atoms in the structure is greater than or equal to 9; and transferring heat to or from the device using the mechanism.

In this disclosure:

"catenated heteroatom" refers to an atom other than carbon (for example, oxygen and nitrogen) that is bonded to carbon atoms in a carbon chain so as to form a carbon-heteroatom-carbon chain;

"device" refers to an object or contrivance which is heated, cooled, or maintained at a predetermined temperature;

"inert" refers to chemical compositions that are generally not chemically reactive under normal conditions of use;

"mechanism" refers to a system of parts or a mechanical appliance; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

The provided hydrofluoroethers provide heat transfer fluids that have surprisingly good thermal stability. They also have high specific heat capacity over a wide range of temperatures, high dielectric strength, low electrical conductivity, chemical inertness, and good environmental properties. The provided hydrofluoroethers can also be useful as components in cleaning solvents, solvents for coating depositions, foam blowing additives, and battery electrolyte solvents.

The above summary is not intended to describe each disclosed embodiment of every implementation of the present invention. The detailed description which follows more particularly exemplifies illustrative embodiments.

DETAILED DESCRIPTION

In the following description, it is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Some hydrofluoroethers have been disclosed as heat-transfer fluids. Exemplary hydrofluoroethers can be found in in U.S. Pat. Publ. Nos. 2007/0267464 (Vitcak et al.) and 2008/0139683 (Flynn et al.), and U.S. Pat. Nos. 7,128,133 and 7,390,427 (Costello et al.) and U.S. Pat. No. 7,988,877 (Flynn et al.). However, the need exists for a heat-transfer fluid which is inert, has high dielectric strength, low electrical conductivity, chemical inertness, thermal stability and effective heat transfer, is liquid over a wide temperature range, has good heat-transfer properties over a wide range of temperatures and also has a reasonably short atmospheric lifetime so that its globalwarming potential is relatively low.

In some embodiments, an apparatus is provided that requires heat transfer. The apparatus includes a device and a mechanism for transferring heat to or from the device using a heat-transfer fluid. Exemplary apparatuses include refrigeration systems, cooling systems, testing equipment, and machining equipment. Other examples include test heads used in automated test equipment for testing the performance of semiconductor dice; wafer chucks used to hold silicon wafers in ashers, etchers, PECVD tools; constant temperature baths, and thermal shock test baths. In yet other embodiments, the provided apparatus can include a centrifugal chiller, a household refrigerator/freezer, an automotive air conditioner, a refrigerated transport vehicle, a heat pump, a supermarket food cooler, a commercial display case, a storage warehouse refrigeration system, a geothermal heating system, a solar heating system, an organic Rankine cycle device, and combinations thereof.

In certain embodiments, the present disclosure includes a device. The device is defined herein as a component, workpiece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In certain embodiments, the present disclosure includes a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in PECVD tools, temperature controlled test heads for die performance testing, temperature controlled work zones within semiconductor process equipment, thermal shock test bath liquid reservoirs, and constant temperature baths. In some systems, such as etchers, ashers, PECVD chambers, and thermal shock testers, the upper desired operating temperature may be as high as 175° C. or even higher.

The heat transfer mechanism includes the provided heat-transfer fluid. The provided heat transfer fluid can be represented by Structure (I):

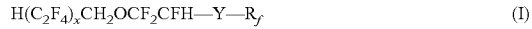

$$H(C_2F_4)_xCH_2OCF_2CFH-Y-R_f \qquad (I)$$

wherein x is a number from 1 to 3. Y can be either a single bond in which case the —CFH group is directly bonded to the —$R_f$ group. Alternatively, Y can represent a single oxygen atom forming an ether linkage between the —CFH group and the —$R_f$ group. When Y is a single bond then $R_f$ is selected from $CF_3$, $C_2F_5$, and $n-C_3F_7$. When Y is a single oxygen atom then $R_f$ can be a linear, branched, or cyclic perfluoroaliphatic group having from 1 to 7 carbon atoms. $R_f$ can also, independently, contain one or more catenated heteroatoms, such as nitrogen or oxygen. The total number of carbon atoms in the heat transfer fluid of Structure (I) is greater than or equal to 9. Typically $R_f$ has zero, one, or two heteroatoms.

When Y is a single oxygen atom, typical $R_f$ groups can include $CF_3$, $C_2F_5$, $n-C_3F_7$, $i-C_3F_7$, $C_4F_9$, $C_5F_{11}$, $CF_3OC_3F_6$, $C_3F_7OCF(CF_3)CF_2$, and $(CF_3)_2NC_3F_6$. $R_f$ groups that include catenated heteroatoms include such moieties as:

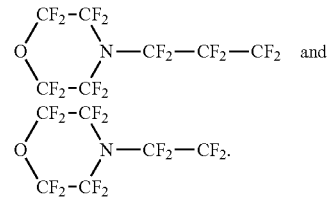

Exemplary fluids have structures such as $H(CF_2CF_2)_3CH_2OCF_2CFHCF_3$ or $HC_6F_{12}CH_2OCF_2CFHOCF_3$.

In some embodiments, a composition of matter is provided that includes a fluid represented by $H(C_2F_4)_xCH_2OCF_2CFH-O-R_f$, wherein x=1-3, wherein, $R_f$ is a linear, branched, or cyclic perfluoroaliphatic group of 1 to 7 carbon atoms which may, independently, contain one or more catenated heteroatoms such as nitrogen or oxygen, and wherein the total number of carbon atoms in the structure is greater than or equal to 9. In some embodiments a fluid is provided that includes $HC_6F_{12}CH_2OCF_2CFHOCF_3$.

Provided hydrofluoroethers of Structure (I) where Y is a single bond can be obtained from the reaction of the corresponding partially fluorinated alcohol $H(C_2F_4)_xCH_2OH$ with a perfluorinated olefin $CF_2=CFR_f$ where x and $R_f$ are defined as above and as exemplified in Example 1 below. Provided hydrofluoroethers where Y is an oxygen atom can be obtained from the reaction of the corresponding partially fluorinated alcohol $H(C_2F_4)_xCH_2OH$ with a perfluorinated vinyl ether $CF_2=CFOR_f$ where x and $R_f$ are defined as above and as exemplified in Example 2 below.

In other embodiments, a method of heat transfer is provided that includes providing a device and a mechanism for transferring heat to or from the device and then transferring heat to or from the device with the mechanism. The heat transfer mechanism includes a heat transfer fluid as represented by Structure (I) with all of the limitations disclosed above. In some embodiments, the transferring of heat by the provided method includes circulating the heat transfer fluid through the device and to or from a chiller, heater, or a combination thereof. In other embodiments, the transferring of heat includes at least partially immersing at least part of the device in the heat transfer fluid.

The provided apparatuses and heat transfer fluids fulfill a market need for a high temperature heat transfer fluid. The provided hydrofluoroethers provide a stable, high temperature heat transfer fluid. In some embodiments, the provided hydrofluoroethers provide a stable, high temperature heat transfer fluid that does not substantially change in purity as measured by gas chromatography/mass spectrometry (CG/MS) when heated and maintained at a temperature of 175° C. for at least 15 days. In some embodiments, the provided hydrofluoroethers provide a stable, high temperature heat transfer fluid that does not substantially change in purity as measured by gas chromatography/mass spectrometry (CG/MS) when heated and maintained at a temperature of 150° C. for at least 36 days. In yet other embodiments, the provided hydrofluoroethers provide a stable, high temperature heat transfer fluid that does not substantially change in purity as measured by gas chromatography/mass spectrometry (CG/MS) when heated and maintained at a temperature of 150° C. for at least 50 days.

The provided hydrofluoroethers also have low toxicity and some of the provided hydrofluoroethers have the ability to pass the regulatory testing that is required to commercialize a new chemical in markets such as the Japanese market which uses the so-called fish bioconcentration tests as described, for example, in N. Yakata et al., *Chemosphere*, 64, (2006), pp. 1885-1891.

Objects and advantages of this invention are further illustrated by the following examples, but the particular materials and amounts thereof recited in these examples, as well as other conditions and details, should not be construed to unduly limit this invention.

EXAMPLES

All parts, percentages, ratios, and the like in the examples are by weight, unless noted otherwise. Solvents and other reagents used were obtained from Sigma-Aldrich Chemical Company, Milwaukee, Wis. unless otherwise noted.

Example 1

Preparation of 7-(1,1,2,3,3,3-hexafluoropropoxy)-1, 1,2,2,3,3,4,4,5,5,6,6-dodecafluoroheptane; $H(CF_2CF_2)_3CH_2OCF_2CFHCF_3$ 2,2,3,3,4,4,5,5,6,6,7,7-dodecafluoroheptan-1-ol (2884 g, 8.68 mol, Daikin, Carrolton, Tex.), acetonitrile (2307 g), potassium carbonate solution (27% w/w, 217 g) were combined in a 2-gallon Parr pressure reactor. The reactor was sealed and the temperature was maintained at 40° C. as hexafluoropropene (1564 g, 10.42 mol, 3M Company, St. Paul, Minn.) was added as a liquid over a period of 20 minutes. The mix was then allowed to stir until no further pressure drop was observed. The mix was emptied, filtered, and acetonitrile was removed by fractional distillation. The product was then treated with anhydrous HF as described in U.S. Pat. No. 7,128,133 (Costello et al.). The excess HF was then neutralized and the product purified by fractional distillation using an Oldershaw column. Product boiling point was 182° C. The product mass was confirmed by GC/MS and purity was measured as 99.82% by $^{13}F$, $^1H$, $^{13}C$ NMR.

An additional purification was carried out by treatment of this ether with potassium permanganate in acetone to remove the last traces of olefinic impurities. Typically this was done batch-wise by refluxing equal volumes of the ether and acetone which contained 1-2% by weight based on ether of potassium permanganate. Water was added, the lower fluorochemical phase separated, and the product was fractionally distilled to remove the remaining acetone, but it was not necessary to distill the product itself beyond this stage.

Stability Testing in Glassware:

Stability testing was carried out by heating of the various samples in clean, PYREX glass round bottom flasks at the temperatures noted below. It was found in the lab that this type of testing proved to be a significantly more severe test than heating the samples in sealed metal tubes and thus provided excellent differentiation among samples.

The stability of $H(CF_2CF_2)_3CH_2OCF_2CFHCF_3$ was tested by placing a portion of the ether, prepared essentially as described in Example 1 and treated with both HF and potassium permanganate, (~100 g) into a new PYREX glass flask containing a reflux condenser under nitrogen and heating to 150° C. for 36 days. Samples of the liquid were taken at 7, 14, 26 and 36 day time intervals and the composition was monitored by GC/MS for breakdown products of the parent molecule. No changes in product purity were observed during the test; that is to say that no new products were seen and the purity of the starting material was unchanged. The compositional analysis (GC/MS and GC-FID) verified this conclusion. After this heating period, the sample was then heated to 180° C. for an additional 14 days. No breakdown products were observed at the end of this time. Monitoring the head space of the flask using a PortaSens HF gas detector probe (manufactured by Analytical Technology Inc.) detected no HF during the entire 50 day heating period.

Example 2

Preparation of $HC_6F_{12}CH_2OCF_2CFHOCF_3$, [1,1,2,2, 3,3,4,4,5,5,6,6-dodecafluoro-7-(1,1,2-trifluoro-2-trifluoromethoxyethoxy)heptane]

Purification of $HC_6F_{12}CH_2OH$:$HC_6F_{12}CH_2OH$ (200 g, 0.602 mole, Daikin, Carrolton, Tex.) was purified to remove the branched-chain isomer $HC_2F_4CH(HC_4F_8)OH$ present in about 5% by reaction with 45% aqueous potassium hydroxide (20 g, 0.16 mole) by heating in a 600 mL Parr reactor to 60° C. for 72 hours. After cooling, the reactor contents were placed into a 1 L flask with the addition of approximately an equal volume of water and the alcohol azeotropically distilled. The isomer content after this treatment was 0.05%.

The purified $HC_6F_{12}CH_2OH$ (50.6 g, 0.152 mole), potassium carbonate (2.9 g, 0.021 mole) and acetonitrile (150 g) were combined in a 600 mL Parr reactor. The reactor was sealed, degassed twice under nitrogen and then evacuated and heated to about 40° C. while trifluoromethyl trifluorovinyl ether ($CF_3OCF=CF_2$, 35.3 g, 0.212 mole, Synquest, Alachua, Fla.) was added in portions over a period of about two hours. The reactor was held at 40° C. for 16 hours and subsequently cooled, vented, and the potassium carbonate removed by filtration. The solvent, acetonitrile, was removed by rotary evaporation followed by the addition of water (400 mL) and the reaction mixture distilled azeotropically using a Dean Stark trap to separate out the lower fluorochemical phase to afford 67.7 g of liquid of 97.4% purity by GLC. This reaction was repeated using 80 g more of the alcohol and the combined azeotropic distillates (174 g) were then fractionated in a concentric tube fractionating unit (Ace Glass, Vineland, N.J., Catalog Number 9331) to give the final product $HC_6F_{12}CH_2OCF_2CFHOCF_3$, 122 g, bp=178° C., 99.2% purity. The structure was consistent with the GC/MS data.

Stability Testing in Glassware;

The stability of $H(CF_2CF_2)_3CH_2OCF_2CFHOCF_3$ was tested by placing a portion of the ether, prepared as described above, (75 g) into a flask containing a reflux condenser under nitrogen and heating while stirring magnetically to 175° C. for 15 days. Samples of the liquid were taken at 1, 2, 3, 4, 7, 8, 9, 11 and 15 day time intervals and analyzed by gas chromatography. In addition, the starting material and the material at the end of the heating period were analyzed by GC/MS for breakdown products of the parent molecule. No changes in product purity were observed by either gas chromatography or GC/MS during the test; that is to say that no new products were seen and the purity of the starting material was unchanged.

Comparative Example 1

The compound 2,3,3,4,4-pentafluoro-2,5-bis(perfluoropropan-2-yl)-5-ethoxytetrahydrofuran (II) was made by the method described in U.S. Publ. No. 2007/0267464 (Vitcak et al.).

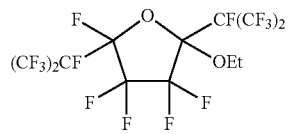

Stability testing in glass was carried out by placing about 100 g of the ether in a 500 mL round bottom flask equipped with a water condenser and heated with magnetic stirring to 150° C. for seven days. Samples of the liquid were taken on days 1, 2, 3, 4, and 7 and analyzed by gas chromatography, HF gas probe, and pH paper. After one day, the pH had dropped from the initial value neutral value of 7 to 5 and remained at that level the remainder of the test. The HF level in the headspace was measured using the PortaSens probe and reached the maximum level which the probe could detect of 27 ppm on day 3 and did not change during the remainder of the test. The decomposition product diketone $(CF_3)_2CFCOC_2F_4COCF(CF_3)_2$ level increased to 1648 ppm on day 7 when the test was terminated. The HF levels in the liquid phase were measured and are shown in the following table.

| Day | ppm F |
|---|---|
| 0 | <0.1 |
| 1 | 1.0 |
| 2 | 1.8 |
| 3 | 2.6 |
| 4 | 3.2 |
| 7 | 3.9 |

Comparative Example 2

Preparation of 3-ethoxy-1,1,1,2,2,3,4,5,5,5-decafluoro-4-(1,1,2,3,3,3-hexafluoro-2-heptafluoropropyloxypropoxy)pentane, $C_3F_7OCF(CF_3)CF_2OCF(CF_3)CF(OC_2H_5)CF_2CF_3$ 1-[1-(difluorotrifluorovinyloxymethyl)-1,2,2,2-tetrafluoroethoxy]-1,1,2,2,3,3,3-heptafluoropropane (216 g, 0.5 mol, Dyneon, Oakdale, Minn.), 2,2,3,3,3-pentafluoropropionyl fluoride (83.3 g, 0.50 mol, 3M Company), potassium fluoride (12.6 g, 0.217 mol, spray dried, Sigma-Aldrich, Milwaukee, Wis.) and diglyme (200 mL) were combined in a 600 mL parr reactor. The mix was heated at 85° C. until the pressure no longer dropped over a 30 min time period. The ketone product that was generated from this reaction (1,1,1,2,2,4,5,5,5-nonafluoro-4-(1,1,2,3,3,3-hexafluoro-2-heptafluoropropyloxypropoxy)-pentan-3-one) was not isolated from the reaction mix. The reaction mixture was emptied into a 3 liter round bottom flask. Diethyl sulfate (92 g, 0.6 mol, Aldrich), potassium fluoride (22.4 g, spray dried, Aldrich) and an additional 1000 mL of diglyme were combined with the reaction mixture. This was heated at 58° C. for 72 hours. Water (350 mL) was then added to the mix and the hydrofluoroether product was steam distilled. A total of 367 g of unpurified HFE was obtained from the alkylation reaction. This was treated with 100 mL of 25% (w/w) KOH at reflux for 1 hour to remove ester impurities. It was then washed with water and dried over anhydrous magnesium sulfate. The product was purified by fractional distillation, b.p.=183° C., purity=99.68%. The product mass was confirmed by GC/MS analysis.

Stability Test of $C_3F_7OCF(CF_3)CF_2OCF(CF_3)CF(OC_2H_5)CF_2CF_3$ 50 grams of the hydrofluoroether was charged to a 50 mL round bottom flask. The material was heated at 150° C. for 8 days with samples taken at day 1, 2, 3, 6, and 8. The primary breakdown product from the parent molecule that was monitored was the ketone intermediate, $C_3F_7OCF(CF_3)CF_2OCF(CF_3)C(O)CF_2CF_3$. This was monitored using GC-FID. The concentration of the ketone increased over a period of 8 days indicating that this HFE was not exceptionally stable to temperatures above 150° C.

| Day | ppm Ketone |
|---|---|
| 1 | 140 |
| 2 | 300 |
| 3 | 503 |
| 6 | 1000 |
| 8 | 1200 |

Comparative Example 3

Preparation of 3-methoxy-1,1,1,2,2,3,4,5,5,5-decafluoro-4-(1,1,2,3,3,3-hexafluoro-2-heptafluoropropyloxypropoxy)pentane—$C_3F_7OCF(CF_3)CF_2OCF(CF_3)CF(OCH_3)CF_2CF_3$ 1-[1-(difluorotrifluorovinyloxymethyl)-1,2,2,2-tetrafluoroethoxy]-1,1,2,2,3,3,3-heptafluoropropane (216 g, 0.5 mol, Dyneon, Oakdale, Minn.), 2,2,3,3,3-pentafluoropropionyl fluoride (83.3 g, 0.50 mol, 3M Company), potassium fluoride (12.6 g, 0.217 mol, spray dried, Sigma-Aldrich, Milwaukee, Wis.) and diglyme (200 mL) were combined in a 600 mL parr reactor. The mix was heated at 85° C. until the pressure no longer dropped over a 30 min time period. The ketone product that was generated from this reaction (1,1,1,2,2,4,5,5,5-nonafluoro-4-(1,1,2,3,3,3-hexafluoro-2-heptafluoropropyloxypropoxy)pentan-3-one) was not isolated from the reaction mix. The reaction mixture was emptied to a 2 liter round bottom flask.

Dimethyl sulfate (76 g, 0.6 mol, Aldrich), potassium fluoride (22.8 g, 0.6 mol, Aldrich) and 500 g of diglyme solvent were combined with the ketone reaction mixture. The mix was heated to 32° C. for 24 hours. 200 mL of water was then added and the product was steam distilled using a Dean-Stark trap. The crude HFE was then refluxed with 30 g of 25% (w/w) KOH solution to remove ester impurities. The product was then washed with water and dried over anhydrous magnesium sulfate. A total of 227 g was recovered and it was purified using fractional distillation. Product boiling point was 175° C. The product mass was confirmed by GC/MS and the purity of the final product was 99.5%.

Stability Test of $C_3F_7OCF(CF_3)CF_2OCF(CF_3)CF(OCH_3)CF_2CF_3$ 50 grams of the hydrofluoroether was charged to a 50 mL round bottom flask. The material was heated at 150° C. for 8 days with samples taken at day 1, 2, 5, 7, and 8. The primary breakdown product from the parent molecule that was monitored was the ketone intermediate, $C_3F_7OCF(CF_3)CF_2OCF(CF_3)C(O)CF_2CF_3$. This was monitored using GC-FID. The concentration of the ketone increased over a period of 8 days indicating that this HFE was not exceptionally stable to temperatures above 150° C.

| Day | ppm Ketone |
| --- | --- |
| 1 | 50 |
| 2 | 50 |
| 5 | 50 |
| 7 | 50 |

Comparative Example 4

Preparation of 1-(1-{[1-(ethoxydifluoromethyl)-1,2,2,2-tetrafluoroethoxy]-difluoromethyl}-1,2,2,2-tetrafluoroethoxy)-1,1,2,2,3,3,4,4,4-nonafluorobutane $C_4F_9OCF(CF_3)CF_2OCF(CF_3)CF_2OC_2H_5$ Preparation of Perfluorobutyryl Fluoride Perfluorobutyryl fluoride was prepared by electrochemical fluorination of isobutyric anhydride in a Simons ECF cell of the type described in U.S. Pat. No. 2,713,593 (Brice et al.) and in R. E. Banks, ed., *Preparation, Properties, and Industrial Applications of Organofluorine Compounds*, Halsted Press (1982), pp. 19-43.

The gaseous products from the cell were further purified by fractional distillation to yield 95% perfluorobutyryl fluoride, 0.8% perfluoro-2-methylpropionyl fluoride and the remainder being perfluorinated inert materials. This mixture could be used in subsequent reactions without further purification. As used herein, the term "perfluorobutyryl fluoride" will refer to the mixture just described.

Preparation of $C_4F_9OCF(CF_3)CF_2OCF(CF_3)CF_2OC_2H_5$

A 600 ml stainless steel jacketed Parr pressure reactor was charged with spray-dried potassium fluoride (4.2 g, 0.072 moles), anhydrous diglyme (103.7 g), ADOGEN 464 solution (10.1 g of solution that was purified by dissolving in diglyme, followed by fractional distillation to remove isopropanol resulting in 48.6% Adogen dissolved in diglyme, 0.0106 moles) and FC-85 (127.5 g, available from 3M Company, St. Paul, Minn.). The vessel was sealed, stirred, cooled to <−10° C. using refrigeration unit, charge with perfluorobutyryl fluoride (79.6 g, 0.350 moles), and held at 14° C. Hexafluoropropene oxide (123 g, 0.741 moles) was continuously charged as a vapor to the reactor over an 8 hour period and then held for 16 hours. The reactor was opened, charged with spray-dried potassium fluoride (22.6 g, 0.389 moles), anhydrous diglyme (106.4 grams), and diethylsulfate (87.2 g, 0.566 moles), sealed, stirred, heated to 52° C. and held for 2 days. Aqueous 45% KOH was charged to the reactor and heated to 65° C. and held for 5 hours. After cooling, the reaction mixture was diluted with 1 L of water allowing the recovery of the bottom product containing phase, 367 g with 28% of the desired material. Another batch was completed using essentially the same prep as above and the combination of these two lots were purified using a 10 perforated plate internal bellows column to afford 58 g containing 98.8% $C_4F_9OCF(CF_3)CF_2OCF(CF_3)CF_2OC_2H_5$ and 0.63% $(CF_3)_2CFCF_2O[CF(CF_3)CF_2O]_2CH_2CH_3$ as determined by NMR.

Stability Test of $C_4F_9OCF(CF_3)CF_2OCF(CF_3)CF_2OC_2H_5$ 50 g of the hydrofluoroether was charged to a 50 mL round bottom flask. The material was heated at 150° C. for 7 days with samples taken at days 3, 5, and 7 days. The primary breakdown products from the parent molecule that were monitored was vinyl ether, $C_4F_9OCF(CF_3)CF_2OCF=CF_2$ and the hydride $C_4F_9OCF(CF_3)CF_2OCFHCF_3$. These were monitored using GC-FID. The concentration of the sum of the two breakdown products are shown in the table below.

| Day | % Breakdown products |
| --- | --- |
| 0 | 0 |
| 3 | 0.18 |
| 5 | 0.32 |
| 7 | 0.49 |

Comparative Example 5

Preparation of 1-{1-[(1-{[1-(ethoxydifluoromethyl)-1,2,2,2-tetrafluoroethoxy]difluoromethyl}-1,2,2,2-tetrafluoroethoxy)difluoromethyl]-1,2,2,2-tetrafluoroethoxy}-1,1,2,2,3,3,3-heptafluoro-propane; $C_3F_7(OCF(CF_3)CF_2)_3OC_2H_5$ This compound was made by alkylation of the corresponding acid fluoride, $C_3F_7(OCF(CF_3)CF_2)_2OCF(CF_3)COF$. The acid fluoride preparation is described in U.S. Pat. No. 3,242,218 (Miller) and U.S. Pat. No. 6,923,921 (Flynn et al.). The alkylation method is described in for example, U.S. Pat. No. 5,750,797 (Vitcak et al.). The compound was further treated with potassium permanganate to remove olefinic impurities.

Stability Test of $C_3F_7(OCF(CF_3)CF_2)_3OC_2H_5$ 50 g of the hydrofluoroether was charged to a 50 mL round bottom flask. The material was heated at 150° C. for 18.75 days with samples taken at days 2.75, 4.75, 6.75, and 18.75 days. The primary breakdown products from the parent molecule that were monitored was vinyl ether, $C_3F_7(OCF(CF_3)CF_2)_2OCF=CF_2$ and the hydride $C_3F_7(OCF(CF_3)CF_2)_2OCFHCF_3$. These were monitored using GC-FID. The concentration of the sum of the two breakdown products are shown in the table below.

| Day | % Breakdown products |
| --- | --- |
| 0 | 0 |
| 2.75 | 0.18 |
| 4.75 | 0.38 |
| 6.75 | 0.45 |
| 9.75 | 0.55 |
| 18.75 | 1.59 |

Example 3

Commercial Chiller Stability Testing at 150° C. for $HC_6F_{12}CH_2OCF_2CFHCF_3$ The long term stability of $HC_6F_{12}CH_2OCF_2CFHCF_3$ in a commercial chiller unit was tested. The chiller used for this test was a Lydall Affinity Chiller, model PWL-003 KBE48CBC3 with an operating range of 10° C. to 200° C. $HC_6F_{12}CH_2OCF_2CFHCF_3$ was circulated through a closed stainless steel loop at 150° C. for 28 days. During this time the chiller operated continuously except for short periods for taking samples in which the fluid was cooled to room temperature before the sample was removed. No performance problems with the chiller were noted. The composition of the circulating fluid was analyzed by GC/MS periodically (on days 1, 3, 6, 13, 20, and 28) to determine whether any changes in the fluid had occurred. Fluorine NMR analysis of the fluid before the testing and after completion of the testing was also carried out. No changes in the composition of the fluid were observed with either NMR or GC/MS. Monitoring the head space of the chiller using a PortaSens HF gas detector probe (manufactured by Analytical Technology Inc.) detected no increase in the HF levels during the entire 28 day heating period. A very small level of HF (1.4 ppm) was observed initially and this value decreased to 0 ppm by day 13. HF was also monitored in the liquid phase by titration and never exceeded a value of 0.52 ppm. The appearance of the metal parts of the chiller was essentially unchanged over the lifetime of the test.

Comparative Example 6

Comparative Commercial Chiller Stability Testing at 150° C.

A comparative hydrofluoroether 2,3,3,4,4-pentafluoro-2,5-bis(perfluoropropan-2-yl)-5-ethoxytetrahydrofuran (II) was also tested multiple times in this same system under the same conditions. The composition of this fluid was monitored periodically over about thirty days for composition changes from the input material. During the course of two of these tests a breakdown product diketone, $(CF_3)_2CFCOC_2F_4COCF(CF_3)_2$ from the parent molecule was observed (range of 24 to 39 ppm at 28 days) which indicated that the parent molecule was not stable at a temperature of 150° C. Much higher values for the diketone were found in other studies ranging from 195 ppm to 472 ppm at 28 days and 7 days respectively. HF was also monitored in the liquid phase by titration and ranged between 0.34 and 0.36 ppm. In marked contrast to that found for $HC_6F_{12}CH_2OCF_2CFHCF_3$, the appearance of the metal parts of the chiller underwent noticeable corrosion. Depending on the study this corrosion varied between quite marked with the formation of black or greenish deposits to less obvious but still showing significant signs of a corrosive agent derived from the fluid. This corrosion as well as the formation of the diketone breakdown product rendered this material unacceptable for use in such a high temperature heat transfer application.

The surprising stability of the provided heat transfer fluids is exemplified by examination of Examples 1-2 and Comparative Examples 1-5. Comparative Examples 1-5 have similar structures to the provided heat transfer fluids of Structure (I) except that they also include an alkoxy group (methoxy or ethoxy). None of the compounds tested in the Comparative Examples have the same stability as the compounds exemplified in Examples 1-2 and which meet the structural requirements of Structure (I).

Furthermore, the heat transfer fluid that includes the hydrofluoroether compound from Example 1 was tested for long term stability in a commercial chiller unit as described in Example 3. The fluid was circulated though a closed stainless steel loop at 150° C. for 28 days with no significant deterioration of the heat transfer fluid during this time. As a comparison, the compound from Comparative Example 1 was put through the same test. In marked contrast, as described in Comparative Example 6, the appearance of the metal parts of the chiller underwent considerable corrosion and was found to have diketone breakdown product which rendered the material unacceptable for use in this application.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. An apparatus requiring heat transfer comprising:
a device; and
a mechanism for transferring heat to or from the device, the mechanism comprising a heat transfer fluid represented by the following structure:

wherein
x=1–3.

2. An apparatus according to claim 1, wherein the structure of the fluid is $HC_6F_{12}CH_2OCF_2CFHOCF_3$.

3. An apparatus according to claim 1, wherein the apparatus is selected from a centrifugal chiller, a household refrigerator/freezer, an automotive air conditioner, a refrigerated transport vehicle, a heat pump, a supermarket food cooler, a commercial display case, a storage warehouse refrigeration system, and a combination thereof.

4. An apparatus according to claim 1, wherein the heat transfer fluid does not substantially change in purity as measured by gas chromatography/mass spectrometry when heated and maintained a temperature of 175° C. for at least 15 days.

5. An apparatus according to claim 4, wherein the heat transfer fluid does not substantially change in purity as measured by gas chromatography/mass spectrometry when heated to a temperature of 150° C. for at least 36 days.

6. An apparatus according to claim 5, wherein the heat transfer fluid does not substantially change in purity as measured by gas chromatography/mass spectrometry when heated to a temperature of 150° C. for at least 50 days.

7. An apparatus according to claim 1, wherein the device comprises a chiller, a heater, or a combination thereof.

8. An apparatus according to claim 1, wherein the heat transfer fluid is a working fluid in an organic Rankine cycle device, geothermal heating system, solar heating system, or a combination thereof.

9. A method of heat transfer comprising:

providing a device and a mechanism for transferring heat to or from the device; the mechanism comprising a heat transfer fluid represented by the following structure:

$$H(C_2F_4)_xCH_2OCF_2CFHOCF_3$$

wherein x=1–3; and transferring heat to or from the device with the mechanism.

10. A method according to claim 9, wherein transferring heat comprises circulating the heat transfer fluid though the device and to or from a chiller, heater, or a combination thereof.

11. A method according to claim 9, wherein transferring heat comprises at least partially immersing at least a part of the device in the heat transfer fluid.

* * * * *